United States Patent [19]

Gutierrez et al.

[11] 4,264,460
[45] Apr. 28, 1981

[54] SUBSTITUTED LACTONE ACID MATERIALS ARE FRICTION MODIFIERS

[75] Inventors: Antonio Gutierrez, Mercerville; Stanley J. Brois, Westfield; Rosemary O'Halloran, Union, all of N.J.

[73] Assignee: Exxon Research & Engineering Co., Florham Park, N.J.

[21] Appl. No.: 951,062

[22] Filed: Oct. 13, 1978

[51] Int. Cl.³ .................. C10M 1/38; C10M 1/20
[52] U.S. Cl. .................. 252/48.6; 252/48.2; 252/49.6; 252/56 R; 252/78.1; 252/47.5; 252/51.5 R
[58] Field of Search .................. 252/48.2, 48.6, 49.6, 252/78.1, 56 R

[56] References Cited

U.S. PATENT DOCUMENTS

| | | |
|---|---|---|
| 2,568,876 | 9/1951 | White et al. .................. 252/51.5 A |
| 2,969,324 | 1/1961 | Knapp, Jr. et al. ............. 252/42.7 X |
| 3,248,187 | 4/1966 | Bell, Jr. ....................... 252/51.5 A X |
| 3,410,801 | 11/1968 | Tunkel et al. ................. 252/33 X |
| 3,520,903 | 7/1970 | Pierce .......................... 252/48.2 X |
| 3,974,081 | 8/1976 | Rutkowski et al. ............ 252/57 X |
| 4,017,406 | 4/1977 | Brois et al. .................... 252/51.5 A |
| 4,029,587 | 6/1977 | Koch ............................ 252/48.2 |
| 4,062,786 | 12/1977 | Brois et al. .................... 252/51.5 A X |
| 4,123,373 | 10/1978 | Brois et al. .................... 252/48.6 |

*Primary Examiner*—Andrew Metz
*Attorney, Agent, or Firm*—Roland A. Dexter; Frank T. Johmann

[57] ABSTRACT

Substituted lactone acid materials are usefully incorporated into an automatic transmission fluid (ATF) in an at least friction modifying amount to provide the ATF with a reduced rate of torque change normally found in ATF formulations when subjected to oxidative conditions. The sulfur-bridged $C_6$–$C_{30}$ alkyl lactone acids are preferred.

7 Claims, No Drawings

SUBSTITUTED LACTONE ACID MATERIALS ARE FRICTION MODIFIERS

BACKGROUND OF THE INVENTION

The present invention relates to an automatic transmission fluid and particularly concerns an additive for such a fluid that will improve its stability against torque degradation while at the same time imparting suitable friction modification. The invention is also directed to additive concentrate packages that are intended for formulation into mineral oil base stocks preferably containing seal swellant to provide transmission fluids of improved stability against oxidative degradation.

A very high percentage of vehicles such as automobiles, tractors and earthmovers are now equipped with some type of semi-automatic or fully automatic transmission. These transmissions must be provided with a supply of fluid that serves the multiple functions of a power transmitting medium, a hydraulic control fluid, a heat transfer medium, and a satisfactory lubricant. A transmission fluid to be useful must be capable of operating over a wide temperature range, possess a high degree of oxidation resistance, be free of corrosive action, have foam control, have satisfactory low temperature fluidity, retain a useful viscosity at high temperatures, have transmission seal compatibility and lubricity without "stick-slip" of the transmission parts.

Exemplary of automatic transmission fluids are those disclosed in U.S. Pat. No. 3,410,801 which is directed to a class of modifiers of the friction characteristics of automatic transmission fluids (hereinafter designated ATF) to reduce squawk and chatter of the transmission; and U.S. Pat. No. 4,017,406 where the carboxylate half esters of 1-aza-3,7-dioxabicyclo[3,3,0]oct-5-yl methyl alcohols are taught in columns 13 and 14 to be useful friction modifiers for ATF.

In U.S. Pat. No. 3,248,187 $C_1$ to $C_{30}$ alkyl substituted acid lactones are taught to be useful as anticorrosion additive for lubricating oils and fuels, said acid lactones prepared by the acid catalytically induced lactonization of alkenyl succinic acid e.g. octadecenyl acid (see column 2, line 70).

The current approach to improving ATF is to adjust and modify the various additives so as to extend their useful lifetime. An additive, such as a friction modifier, which would operate as a functional additive while providing activity to limit the functional degradation of the ATF is desirable.

Recently published U.S. Pat. No. 4,062,786 teaches of chemical and oxidatively stable lactone oxazoline reaction products of hydrocarbon substituted lactone carboxylic acids, e.g. lactonized 2-octadecenyl succinic anhydride with a 2,2-disubstituted-2-amino-1-alkanol which are reported to be useful as sludge dispersants for lubricating oil or antirust agents for gasoline.

SUMMARY OF THE INVENTION

In accordance with the present invention, it has been found that automatic transmission fluids, preferably containing a seal swellant, can be provided with enhanced oxidation stability by the incorporation of a friction modifier which is a substituted lactone acid material, i.e. acid, ester or amide, which can be represented in part by the formula:

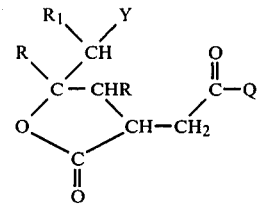

wherein R is selected from the group consisting of hydrogen and alkyl radicals containing from 1 to 5 carbons, $R_1$ is a normal hydrocarbon, preferably an alkyl group ranging from 6 to 30 carbons, Q is selected from hydroxyl, alkoxy of from 1 to 5 carbons and dialkyl amino wherein said alkyl group contains 1 to 6 carbons, and Y is selected from the group consisting of hydrogen, hydroxyl, sulfo, alkylthio (TS—), alkyldithio (TSS—), and a sulfur bridge, e.g. —S— and —S—S—, joining two lactone units together as depicted below wherein z is a number ranging from 1 to 4 and T is defined hereafter as containing 1 to 50, preferably 2 to 20 carbons; Q preferably is OH.

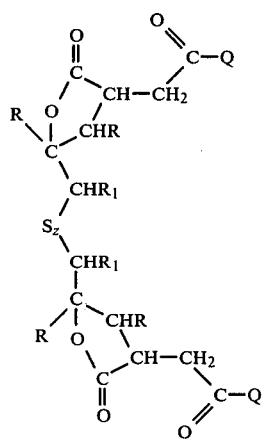

Particularly preferred are those sulfur-bridged lactone acids wherein R is defined by lactonized octadecenyl succinic anhydride which for purposes of this disclosure is 6,6'-di-thio-bis-(3,5carbolactone-1-heneicosanoic acid).

The fully formulated automatic transmission fluid usefully contains from 0.01 to 1, preferably 0.03 to 0.8, optimally 0.5, of the novel and oxidatively stable lactone acid friction modifier. The ATF package will generally contain from 40 to 60 weight percent synthetic or mineral oil and from 0.1 to 10, preferably 0.3 to 8 weight percent of the friction modifier of this invention, said weight percents being based on the total weight of said package. In the preferred ATF formulations there is contained in addition to the friction modifier a substantially identical weight of seal swellant although the amount can usefully range from 50% to 150% of the weight of said friction modifier.

DESCRIPTION OF THE PREFERRED EMBODIMENTS OF THE INVENTION

ATF systems are compounded from a number of additives each useful for improving a chemical and/or physical property of the ATF. The additives are usually sold as a package in which mineral oil is present. The mineral lubricating oil will constitute from 40 to 60 weight percent of the package and is a refined hydrocarbon oil or a mixture of refined hydrocarbon oils selected according to the vicosity requirements of the particular ATF but typically would have a viscosity range of 75-150 SSU at 37.8° C. Additives present in such packages include viscosity index improvers, corrosion inhibitors, oxidation inhibitors, friction modifiers, dispersants, de-emulsifiers, antifoaming agents, antiwear agents, pour point depressants and seal swellants.

The viscosity index improvers that may be employed in the ATF of this invention include any of the types known to the art including polyisobutylene, copolymers of ethylene and propylene, polymethacrylates, methacrylate copolymers, copolymers of an unsaturated dicarboxylic acid and a vinyl compound and interpolymers of styrene and acrylic esters.

Corrosion inhibitors also known as anticorrosive agents reduce the degradation of the metallic parts contained by the ATF. Illustrative of corrosion inhibitors is zinc dialkyl dithiophosphate, phosphosulfurized hydrocarbons and the products obtained by reaction of a phosphosulfurized hydrocarbon with an alkaline earth metal oxide or hydroxide, preferably in the presence of an alkylated phenol or of an alkyl phenol thioether, and also preferably in the presence of carbon dioxide. Phosphosulfurized hydrocarbons are prepared by reacting a suitable hydrocarbon such as a terpene, a heavy petroleum fraction or a $C_2$ to $C_6$ olefin polymer such as polyisobutylene with from 5 to 30 weight percent of a sulfide of phosphorus for ½ to 15 hours, at a temperature in the range of 150° C. to 600° F. Neutralization of the phosphosulfurized hydrocarbon may be effected in the manner taught in U.S. Pat. No. 2,969,324.

Oxidation inhibitors reduce the tendency of mineral oils to deteriorate in service which deterioration is evidenced the products of oxidation such as sludge and varnish-like deposits on the metal surfaces. Such oxidation inhibitors include alkaline earth metal salts of alkyl phenol thioethers having preferably $C_5$ to $C_{12}$ alkyl side chains, e.g. calcium nonyl phenol sulfide, barium t-octyl phenol sulfide, zinc dialkyl dithiophosphates, dioctyl diphenyl amine, phenyl alpha naphthylamine, phosphosulfurized or sulfurized hydrocarbons, etc.

Dispersants maintain oil insolubles resulting from oxidation during use in suspension in ATF thus preventing sludge flocculation and precipitation. Suitable dispersants include high molecular weight alkyl succinates, the reaction product of polyisobutylene-succinic anhydride with tetraethylene penta-amine and borated salts thereof.

Pour point depressants lower the temperature at which the ATF will flow or can be poured. Such depressants are well known. Typical of those additives which usefully optimize the low temperature fluidity of the ATF of the invention are $C_8$-$C_{18}$ dialkyl fumarate vinyl acetate copolymers, polymethacrylates, and wax naphthalene condensation products.

A de-emulsifier suitable for the teachings of this disclosure is a commercially available blend of oxyalkylated materials sold as Breaxit 7937 by Exxon Chemical Company, U.S.A., Houston, Texas.

Foam control is provided by an anti-foamant of the polysiloxane type, e.g. silicone oil and polydimethyl siloxane.

Antiwear agents as their name implies reduce wear of the transmission parts. Representative of suitable antiwear agents are zinc dialkyl dithiophosphate, zinc diaryl dithiophosphate and magnesium sulfonate.

Some of these numerous additives can provide a multiplicity of affects, e.g. a dispersant-oxidation inhibitor. This approach is well known and need not be further elaborated herein.

Seal swellants which are present in combination with the friction modifier of the invention include mineral oils of the type that provoke swelling and aliphatic alcohols of 8 to 13 carbon atoms such as tridecyl alcohol with a preferred seal swellant being characterized as an oil-soluble, saturated, aliphatic or aromatic hydrocarbon ester of from 10 to 60 carbon atoms and 2 to 4 ester linkages, e.g. dihexyl phthalate, as are described in U.S. Pat. No. 3,974,081.

The additives of this invention which have utility as friction modifiers are alkyl and heterosubstituted lactone acid materials, i.e. acids, esters and amides.

The preparation of these useful lactone acids involves a lactonization of an alkenyl succinic acid analog obtained via the Ene reaction of an olefin with an alphabeta unsaturated $C_4$ to $C_{10}$ dicarboxylic acid, or anhydrides or esters thereof, such as fumaric acid, itaconic acid, maleic acid, maleic anhydride, dimethyl fumarate, etc. The dicarboxylic acid material can be illustrated by an alkenyl substituted anhydride which may contain a single alkenyl radical or a mixture of alkenyl radicals variously bonded to the cyclic succinic anhydride group, and is understood to comprise such structures as:

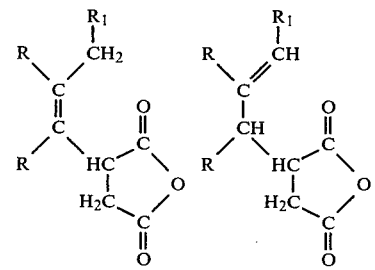

wherein R may be hydrogen or simple alkyl and $R_1$ is a normal hydrocarbyl or substituted normal hydrocarbyl group having from 10 to about 36 carbons, and preferably from 12 to about 26 carbon atoms. The anhydrides can be obtained by well-known methods, such as the reaction between an olefin and maleic anhydride or halosuccinic anhydride or succinic ester (U.S. Pat. No. 2,568,876). However, the exact structure may not always be ascertained and the various R and $R_1$ groups cannot always be precisely defined in the Ene products from polyolefins and maleic anhydride.

Suitable olefins include butene, isobutene, pentene, decene, dodecene, tetradecene, hexadecene, octadecene, eicosene, and polymers of propylene, butene, isobutene, pentene, decene and the like, and halogen-containing olefins. The olefins may also contain cycloalkyl and aromatic groups. The most preferred alkenyl succinic anhydrides used in this invention are those in which the alkenyl group contains a total of from 10 to 36 carbon atoms, preferably from 12 to about 26 carbon atoms.

Many of these hydrocarbyl substituted dicarboxylic acid materials and their preparation are well known in the art as well as being commercially available, e.g., 2-octadecenyl succinic anhydride and polyisobutenyl succinic anhydride.

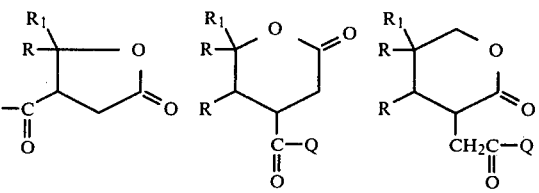

With 2-chloromaleic anhydride and related acylating agents, alkenylmaleic anhydride reactants are formed. Lactonization of these products also afford useful precursors to lactone acid materials.

Preferred olefin polymers for reaction with the unsaturated dicarboxylic acids are polymers comprising a major molar amount of $C_2$ to $C_5$ monoolefin, e.g., ethylene, propylene, butylene, isobutylene and pentene. The polymers can be homopolymers such as polyisobutylene, as well as copolymers of two or more of such olefins such as copolymers of: ethylene and propylene; and, butylene and isobutylene.

Unsubstituted or simple lactone reactants (Y=H) are readily obtained by the acid-catalyzed lactonization of an alkenyl dicarboxylic acid analog, the latter being derived from the ring scission of an alkenyl succinic anhydride with water, an alcohol or an amine as shown below wherein HQ represents water, alcohols containing from 1 to 5 carbons and dialkyl amines containing from 2 to 12 carbons and R and $R_1$ are as previously defined.

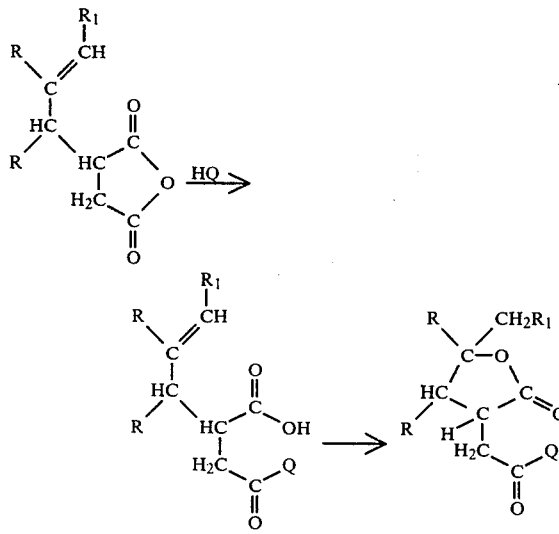

The reaction with HQ is assumed to open the anhydride at the least congested carbonyl group and form a succinic acid, hemi-ester or amic acid product which in the presence of an acid catalyst cyclizes mostly to the 5-ring lactone product as shown above.

It is possible to use alkenyl substituents with the double bond in the 1, 2, or 3-position or even double bonds further out on the hydrocarbyl chain since the acid catalyst is capable of moving it into a position suitable for lactone formation. In general, the size of the lactone ring formed will depend upon, inter alia, the position of the double bond, and which carboxylic acid group participates in the lactone forming reaction. As a consequence, both 5- and 6-ring (or larger ring) lactones can be envisaged as illustrated below:

For convenience, the products of the present invention are usually shown as 5-ring lactones although larger ring lactone products can also be present.

The presence of certain heteroatoms adjacent to the lactone ring of times endows the lactone system with other desirable properties such as antioxidation and anti-corrosion activity and in fact, the sulfur-bridged lactone acid is the preferred ATF additive. It is within the scope of this invention to utilize lactone acid additives having hydroxyl, thiyl, sulfide, sulfoxide, sulfone and sulfo groups adjacent to the lactone acid function as described below:

Hydroxyl containing lactone reactants are prepared via the addition of peracids, hydrocarbyl peroxides or aqueous hydrogen peroxide to alkenyl succinic acid, hemiester or amide reagents as shown below:

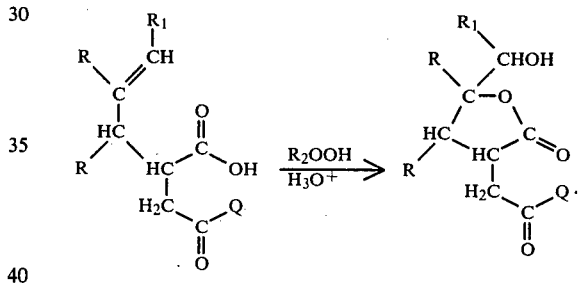

wherein Q, R and $R_1$ are as previously defined and $R_2$ represents hydrogen, acyl group containing from 8 to 30 carbons or alkyl group containing from 8 to 30 carbons. As an alternate, the epoxidation of alkenyl succinic anhydride, with peracids gives epoxy anhydrides which can react with water, alcohols or amines to generate the desired hydroxy-substituted lactone acid end product.

The thiyl substituted lactone acids can be conveniently prepared via sulfenyl halide addition to the double bond in alkenyl succinic acids or esters followed by lactonization via an internal displacement of halide as shown below:

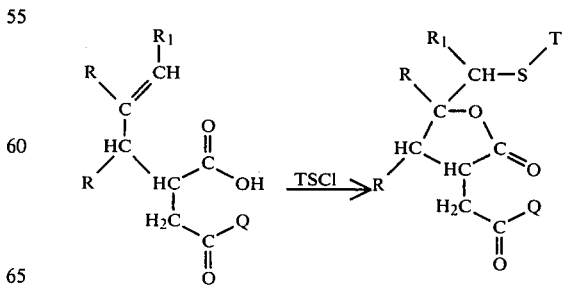

wherein T represents alkyl, aryl or heterocyclic groups containing from 1 to 50 carbons.

The type of thiyl substituted lactone product will depend upon the mode of addition of the sulfenyl chloride to the double bond in the alkenyl succinic acid, ester or amide reactant.

With sulfur halides ($S_xCl_2$, where x is 1–4), thio, dithio and polythio bis-lactones are formed.

Oxidation of the mono-thio-bis-lactones with peroxides can yield both sulfoxides and sulfones. In the case of the dithio-bis-lactones, oxidation affords sulfo-containing lactones.

In another approach thiyl lactones can also be designed by addition of the sulfenyl chloride reagent to the alkenyl succinic anhydride. Lactonization of the adduct can then be effected by either reacting (i) the sulfenyl chloride adduct per se, or (ii) the dehydrohalogenated adduct with an alcohol, water or an amine. Lactonization of the dehydrohalogenated thiyl substituted anhydride via option (ii) is preferably conducted in the presence of an acid catalyst.

Examples of useful sulfenyl chlorides in preparing thiyl lactones include sulfenyl chloride derivatives of alkyl and aryl thiols, and heterocyclic thiols such as 2-mercaptobenzothiazole. Dithiophosphoric acids e.g. $(RO)_2P(=S)$—SH, when converted to the corresponding sulfenyl chloride analog, are also useful in designing phosphorus-containing products.

In another embodiment of the present invention, the reaction of chlorosulfonic acid or its equivalent, e.g. $SO_3$ and its complexes, with alkenylsuccinic anhydrides gives adducts which upon hydration yield sulfo lactone acids.

The intramolecular cyclization, i.e. lactonization, must be carried out in the presence of an acid-type catalyst in order to effect formation of the lactone. Suitable catalysts include the mineral acids such as sulfuric acid, the sulfonic acids such as the alkanesulfonic acids; the Lewis type acids such as aluminum chloride, and low molecular weight sulfonic acid type ion exchange resin materials, such as cross-linked sulfonated polystyrene which is commercially available as Dowex-50. The amount of catalyst present in the reaction zone can be varied over wide limits depending upon the nature of the reactants and the catalyst used. The amount of catalyst used is also determined to a considerable extent by the temperature selected for conducting the reaction. Thus, at higher temperatures the amount of catalyst required in the reaction is less than when lower temperatures are used. Ordinarily, the amount of catalyst used will be between about 0.1% up to 10% by weight of the amount of the alkenyl succinic anhydride reactant.

The friction modifiers taught herein to be useful in ATF can be used also or preferably in combination with a seal swellant in amounts ranging from 0.01 to 1 wt.%.

Fully formulated ATF compositions contain many additives which are typically blended at the following range of treating levels.

| Components | Concentration Range, Volume % |
| --- | --- |
| Viscosity Index Improver | 1–15 |
| Corrosion Inhibitor | 0.01–1 |
| Oxidation Inhibitor | 0.01–1 |
| Friction Modifier | 0.01–1 |
| Dispersant | 0.5–10 |
| Pour Point Depressant | 0.01–1 |
| De-emulsifier | 0.001–0.1 |
| Antifoaming Agent | 0.001–0.1 |
| Antiwear Agent | 0.001–1 |
| Seal Swellant (100% active) | 0.1–5 |

The nature of this invention may be better understood when reference is made to the following Examples:

EXAMPLE 1

3,5-CARBOLACTONE-1-HENEICOSANOIC ACID

This is lactonized-2-octadecenyl succinic acid which is prepared as follows: A half mole (175 g) of 2-octadecenyl succinic anhydride and 0.55 mole (10 g) of water were mixed and heated in a reaction flask for a half hour at 80° C. Infrared analysis showed that complete conversion of the anhydride to succinic acid had occurred. While stirring at 80° C., 0.5 g of concentration sulfuric acid was added, and the reaction temperature was increased to 130°–140° C. Heating at 140° C. for 1.5 hours completely converted the di-carboxylic acid to the desired lactone acid products. When the cooled mixture was diluted with ether, a white solid separated from solution. Infrared analysis of the isolated solids revealed the presence of a 5-ring lactone acid (strong bands at 5.67 and 5.82 microns). Cooling the supernatant gave more solids. Further fractional crystallization of later crops afforded 6-ring lactone acid products. The combined weight of all crops revealed that the yield of lactone acid product was quantitative. A recrystallized sample of 5-ring lactone product melted at 112° C. and analyzed for 71.50% carbon, 10.77% H and 16.67% oxygen. Theory requires 71.49% C, 11.18% H, and 17.32% O.

EXAMPLE 2

6,6'-THIO-BIS-(3,5-CARBOLACTONE-1-HENEICOSANOIC ACID)

This product is prepared by sulfenylating and lactonizing 2-octadecenyl succinic acid in the manner described below.

Two-tenths mole (73.6 g) of octadecenyl succinic acid was dissolved in 500 ml ether and a tenth mole (10.3 g) of $SCl_2$ was added dropwise to the stirred ether solution at about 25° C. The addition was exothermic (ether refluxed) and HCl evolution occurred. The mixture was refluxed for about 8 hours. Upon cooling, solids separated from solution. The solid product featured an infrared spectrum with prominent lactone and carboxylic acid carbonyl absorptions at 5.62 and 5.82 microns, melted at 158°–163°, and analyzed for 69.01% C, 10.17% H, 4.37% S and 16.74% O. Theory for the lactone acid ($C_{44}H_{78}O_8S$) requires 68.88% C, 10.25% H, 4.18% S and 16.69% O.

Further refluxing the supernatant gave four more crops of product with a combined weight of 50 g. The yields were quantitative. The proposed structure for the product is illustrated below.

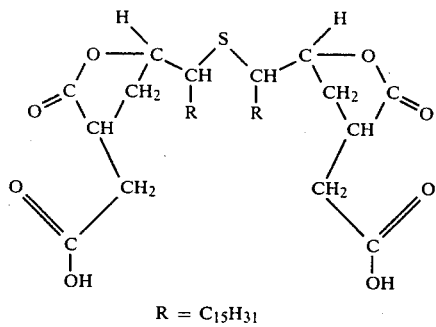

R = C₁₅H₃₁

EXAMPLE 3.

6,6'-DITHIO-BIS-(3,5-CARBOLACTONE-1-HENEICOSANOIC ACID)

This product is designed by successively chlorosulfenylating and lactonizing 2-octadecenyl succinic acid in the manner described below.

Two-hundred grams (0.54 mole) of n-octadecenyl succinic acid were dissolved in a liter of $CHCl_3$ and 36.7 g (0.272 mole) of sulfur monochloride ($S_2Cl_2$) were added dropwise to the stirred solution at room temperature. The exothermic process was accompanied by vigorous HCl evolution. After refluxing the mixture for about 8 hours, the solution was cooled and solids separated. Filtration gave 19 g of solid (m.p. 131°–136° C.) which featured an IR spectrum with intense carbonyl bands at 5.62 and 5.72 microns, and analyzed for 66.42% C, 9.63% H, and 8.22% S. Theory for the adduct ($C_{44}H_{78}O_8S_2$) requires 66.12% C, 9.84% H, and 8.02% S. Rotoevaporation of the supernatant gave more solid product in high yield. The proposed structure for the product is given below.

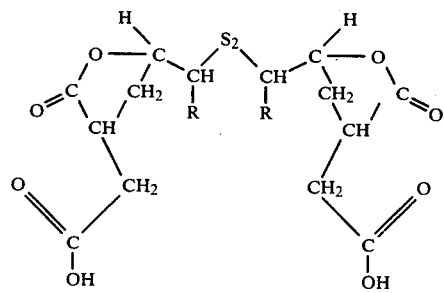

R = n-C₁₅H₃₁

EXAMPLE 4

One method of evaluating the utility of a friction modifier in ATF is to compare the performance under mild oxidation conditions of an ATF containing the additive with a commercial additive having the same formulation but with a common amount of a different friction modifier.

The test utilized a SAE No. 2 Machine described in Dexron Automatic Transmission Fluid Specification of April, 1967 published by the Fuels and Lubricants Dept., Research Laboratories, General Motors Corp., Warren, Michigan. One test quart of ATF is subjected repeatedly to buildup between the engagement of a clutch pack consisting of 4 steel plates and 2 friction plates SD 715. The oil temperature usually reaches from 115° C. to 121° C.

The fresh test sample was subjected to measurement of Δ (delta torque, i.e. midpoint torque subtracted from static torque, at 150, 200 and 250 cycles. The sample then was held for 48 hours at 116° C. with air blowing and again subjected to Δ torque measurement at said 150, 200 and 250 cycles on fresh plates. The conditions of the series of tests are for the:

| (a) Stabilization Cycle | |
|---|---|
| RPM | 3600 |
| Inertia, ft. lb. | 16,500 |
| No. of Cycles | 150 |
| Oil Temp., °F. | 275 ± 3 |
| Lockup Time, sec. | 1.00 ± 0.02 |
| Lockup Pressure | Variable; |
| (b) Friction Characteristics Cycle | |
| RPM | 3600 |
| Inertia, ft. lb. | 7200 |
| No. of Cycles | 50 |
| Oil Temp., °F. | 240± 2 |
| Lockup Time, sec. | Variable |
| Piston Apply Pressure, lbs. | 40; |
| and | |
| (c) High Energy Stabilization | |
| RPM | 3600 |
| Inertia, ft. lb. | 16,500 |
| No. of Cycles | 50 |
| Oil Temp., °F. | 275 ± 3 |
| Piston Apply Pressure, lbs. | 60 |
| Lockup Time, sec. | Variable. |

Three samples of ATF were tested by comparing a commercially available ATF package Paranox 415 (this contains 0.2 wt.% friction modifier) sold by Exxon Chemical Co. of Houston, Texas (Test Sample 1) with the friction modifiers of Ex. 1 and Ex. 3 of this specification by replacing the friction modifier of said Paranox 415 with an equal weight of said product of Ex. 1 (Test Sample 2) and with an equal weight of said product of Ex. 3 (Test Sample 3). The results are set forth in the following Table.

It is desirable that the ATF show a rounded curve on lockup, i.e. a small positive or, preferably negative Δ torque (midpoint to static) and that that character of Δ torque should change as little as possible with aging.

TABLE

Friction Tests On ATF In SAE No. 2 Machine

| | TEST SAMPLE | | |
|---|---|---|---|
| | 1 (Paranox 415) | 2 Friction Modifier is Prod. of Ex. 1 | 3 Friction Modifier is Prod. of Ex. 3 |
| Fresh ATF | | | |
| 150 cycles,Pressure lbs.[1] | 44 | 40.5 | 40 |
| Δ Torque | −2 | +5 | −1 |
| 200 cycles shift,seconds[2] | 0.42 | 0.41 | 0.40 |
| Δ Torque | −3 | −2 | −1 |
| 250 cycles shift,seconds[2] | 0.74 | 0.73 | 0.70 |
| Δ Torque | −2 | +4 | +4 |
| Sum of Δ Torques | −7 | +7 | +2 |
| Oxidized Fluid | | | |
| 150 cycle Pressure,lbs.[1] | 39 | 40 | 41.5 |
| Δ Torques | +7 | +4 | +1 |
| 200 cycles shift,seconds[2] | 0.40 | 0.41 | 0.43 |
| Δ Torque | +3 | +1 | −2 |
| 250 cycles shift,seconds[2] | 0.67 | 0.69 | 0.71 |
| Δ Torque | +12 | +9 | +5 |
| Sum of Δ Torques | +22 | +14 | +4 |
| Change in Sum of Δ Torques | 29 | 7 | 2 |

| | Friction Tests On ATF In SAE No. 2 Machine | | |
|---|---|---|---|
| | TEST SAMPLE | | |
| | 1 (Paranox 415) | 2 Friction Modifier is Prod. of Ex. 1 | 3 Friction Modifier is Prod. of Ex. 3 |
| upon oxidation | | | |

¹pressure required for 1 second shift
²time required to complete shift pattern

The data of the Table shows that the ATF containing a friction modifier according to this invention is both useful and has improved resistance to friction degradation than a commercially available ATF, i.e. less tendency to deteriorate (become positive in torque) on aging.

Representative of the additive packages provided under the teachings herein are the following concentrate blends:

| | Vol. % in Package | | |
|---|---|---|---|
| Component (Additive) | A | B | C |
| Mineral Oil | 14 | 35 | 76 |
| Vis. Index Improver | 24 | 40 | 8 |
| Corrosion Inhibitor | 3 | 2 | 1 |
| Oxidation Inhibitor | 3 | 2 | 1 |
| Friction Modifier | 3 | — | 1 |
| Seal Swellant | 23 | 4 | 5 |
| Dispersant | 27 | 15 | 8 |
| De-emulsifier | — | — | 0.1 |
| Antifoaming Agent | 0.02 | 0.02 | 0.005 |
| Antiwear Agent | 3 | 2 | — |

In such additive packages the range of synthetic or mineral oil diluent for highly concentrated packages ranges from 10 to 40 percent of the total volume, in moderately concentrated packages from 40 to 60 percent of the total volume; and in dilute packages and ATF from 60 to 95 percent of the total volume. Thus said diluent oil ranges overall from 10 to 95 percent of the total volume.

A useful ATF is represented by the following formulation:

| Additive Type | Compound | Amount % |
|---|---|---|
| Diluent/Base Oil | Mineral Oil (100 neutral) | 94.2 |
| Viscosity Index Improver | polymethacrylate | 1.0 |
| Corrosion Inhibitor | phosphosulfurized terpene | 0.3 |
| Oxidation Inhibitor | phenyl alpha naphthylamine | 0.3 |
| Friction Modifier | 6,6'-dithio-bis (3,5-carbolactone-1-heneicosanoic acid) | 0.4 |
| Seal swellant | dihexyl phthalate | 2.0 |
| Dispersant | amidated polyisobutylene succinate | 1.5 |
| Antiwear agent | zinc dialkyl dithio phosphate | 0.3 |
| Antifoamant | polydimethyl siloxane | 0.002 |

The volume percentages as used herein are all calculated at ambient temperatures and values are based on the total composition volume.

The ATF formulation earlier set forth is merely illustrative of a transmission fluid which could be useful for automatic transmissions as found on automobiles and trucks, power transmissions as found on farm equipment and earth movers, wet brakes and in rotary engines of the Wankel type in which the same fluid could be used for both lubrication and power transmission. Such formulations can vary in content and type of additives in a manner shown by the illustrative packages. Similarly these illustrative packages may otherwise vary in the number of blended additives, e.g. oftentimes the viscosity index improver is not present in the additive package. In a preferred system of packages and ATF, the friction modifier of the invention is blended with the seal swellant in a mineral oil base stock.

The invention in its broader aspect is not limited to the specific details shown and described and departures may be made from such details without departing from the principles of the invention and without sacrificing its chief advantages.

What is claimed is:

1. An automatic transmission fluid comprising a synthetic or mineral lubricating oil base formulated with automatic transmission fluid additives and at least a friction modifying amount of a substituted lactone acid material represented by the formula

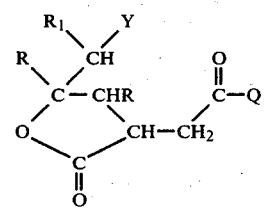

wherein: R is selected from the group consisting of hydrogen and alkyl radicals containing from 1 to 5 carbons; $R_1$ is selected from a normal hydrocarbon group ranging from 6 to 30 carbons; Q is selected from hydroxyl, alkoxy of from 1 to 5 carbons and dialkylamino wherein said alkyl group contains 1 to 6 carbons; and, Y is selected from the group consisting of hydroxyl, sulfo, alkylthio, alkyldithio and a sulfur bridge comprising one to about four sulfur atoms joining two lactone units together: whereby said fluid is provided with a reduced rate of torque change when employed as an automatic transmission fluid subjected to oxidative conditions.

2. A fluid according to claim 1 wherein said fluid contains at least a seal swelling amount of a seal swellant.

3. A fluid according to claim 1 wherein said substituted lactone acid material is of the formula

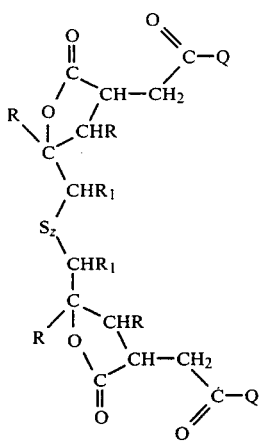

wherein Z is 1 to 4.

4. A fluid according to claim 3 wherein said sulfur-bridged lactone acid is 6,6'-dithio-bis-(3,5-carbolactone-1-heneicosanoic acid).

5. The fluid of claim 2 wherein there is also present an inhibiting amount of a corrosion inhibitor, an inhibiting amount of an oxidation inhibitor, a dispersing amount of a dispersant, and an antifoaming amount of a siloxane.

6. A method of reducing the rate of torque change of the fluid or oxidation in an automatic transmission, said fluid having a mineral lubricating oil base which comprises adding to said transmission fluid at least a friction modifying amount of a sulfur-bridged substituted lactone acid material represented by the formula

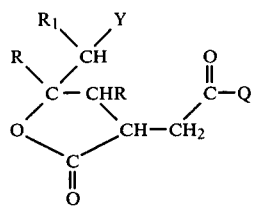

wherein: R is selected from the group consisting of hydrogen and alkyl radicals containing from 1 to 5 carbons; $R_1$ is selected from a normal hydrocarbon group ranging from 6 to 30 carbons; Q is selected from hydroxyl, alkoxy of from 1 to 5 carbons and dialkylamino wherein said alkyl group contains 1 to 6 carbons; and, Y is a sultur bridge comprising one to about four sulfur atoms joining two lactone units together.

7. A method according to claim 6 wherein said acid is 6,6'-dithio-bis-(3,5-carbolactone-1-heneicosanoic acid).

* * * * *